(12) United States Patent
Westermann et al.

(10) Patent No.: US 7,595,418 B2
(45) Date of Patent: Sep. 29, 2009

(54) PROTECTED 5,7-DIHYDROXY-4,4-DIMETHYL-3-OXOHEPTANOIC ACID ESTERS AND 5,7-DIHYDROXY-2-ALKYL-4,4-DIMETHYL-3-OXOHEPTANOCI ACID ESTERS FOR THE SYNTHESIZING OF EPOTHILONE AND EPOTHILONE DERIVATIVES AND PROCESS FOR THE PRODUCTION OF THESE ESTERS

(75) Inventors: Juergen Westermann, Berlin (DE); Johannes Platzek, Berlin (DE); Orlin Petrov, Berlin (DE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 160 days.

(21) Appl. No.: 10/559,389

(22) PCT Filed: Jun. 5, 2004

(86) PCT No.: PCT/EP2004/006057

§ 371 (c)(1),
(2), (4) Date: Mar. 16, 2007

(87) PCT Pub. No.: WO2004/108697

PCT Pub. Date: Dec. 16, 2004

(65) Prior Publication Data

US 2008/0015366 A1    Jan. 17, 2008

(30) Foreign Application Priority Data

Jun. 7, 2003 (DE) .................................. 103 26 195

(51) Int. Cl.
*C07C 255/00* (2006.01)
(52) U.S. Cl. .................... 558/398; 558/435; 558/441
(58) Field of Classification Search ................. 558/398, 558/435, 441
See application file for complete search history.

(56) References Cited

U.S. PATENT DOCUMENTS

| 6,211,412 B1 | 4/2001 | Georg et al. |
|---|---|---|
| 2003/0158412 A1 | 8/2003 | Westermann |
| 2003/0176710 A1 | 9/2003 | Klar |

FOREIGN PATENT DOCUMENTS

| DE | 10041470 | * | 2/2002 |
|---|---|---|---|
| WO | WO 0058254 | | 10/2000 |
| WO | WO 03014063 | | 2/2003 |
| WO | WO 03053949 | | 7/2003 |

OTHER PUBLICATIONS

Database Beilstein Beilstein Institute for Organic Chemistry, Frankfurt-main, DF Beilstein Reaction ID 4276427 XP002301163 vol. 46(4), pp. 559-571, 1998.

* cited by examiner

*Primary Examiner*—D. Margaret Seaman
*Assistant Examiner*—Nizal S Chandrakumar

(57) ABSTRACT

This invention describes protected 5,7-dihydroxy-4,4-dimethyl-3-oxoheptanoic acid ester and 5,7-dihydroxy-2-alkyl-4,4-dimethyl-3-oxoheptanoic acid ester for the synthesis of epothilones and epothilone derivatives and process for the production of these esters.

4 Claims, No Drawings

PROTECTED 5,7-DIHYDROXY-4,4-DIMETHYL-3-OXOHEPTANOIC ACID ESTERS AND 5,7-DIHYDROXY-2-ALKYL-4,4-DIMETHYL-3-OXOHEPTANOCI ACID ESTERS FOR THE SYNTHESIZING OF EPOTHILONE AND EPOTHILONE DERIVATIVES AND PROCESS FOR THE PRODUCTION OF THESE ESTERS

INTRODUCTION

The invention relates to protected 5,7-dihydroxy-4,4-dimethyl-3-oxoheptanoic acid ester and 5,7-dihydroxy-2-alkyl-4,4-dimethyl-3-oxoheptanoic acid ester for the synthesis of epothilones and epothilone derivatives and process for the production of these esters, i.e., new intermediate products and process for their production and the use.

The process for the production of new intermediate products starts from economical starting materials, yields the intermediate products in high enantiomer purities, in high chemical purity, in good yields, and allows production on an industrial scale.

The invention is used in the synthesis of the C1-C6 segment that is required for the production of natural and synthetically modified epothilones or derivatives.

The natural epothilones are 16-membered macrolide rings, which were isolated from cultures of the myxobacterium sporangium cellosum, and are representatives of a class of promising anti-tumor agents that were tested and found to be effective against a number of cancer lines.

A survey of the syntheses primarily of natural epothilones has been described by J. Mulzer et al. in J. Org. Chem. 2000, 65, 7456-7467.

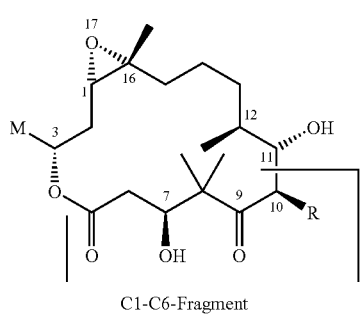

C1-C6-Fragment

In the literature, in addition to the natural epothilones, a number of synthetic epothilone derivatives are described, which for the most part vary within radicals M and $R^{10}$ (for example in WO99/01124, WO 99/02541, WO 0037473, WO 0099/07692, WO 0099/47584, WO 00/49021, WO 01/81342, WO 00/66589, WO 01/81341). Here, in most cases, M stands for a heterocyclic radical and R stands for an alkyl radical. Most syntheses of natural epothilones and the synthetic epothilone derivatives use the A-component fragment, which introduces the carbon atom $C_5$-$C_{10}$ into the macrolide. Within this epothilone segment C1-C6, $C_1$ is the $C_5$ in the macrolide, and $C_6$ is the $C_{10}$ in the macrolide, etc.

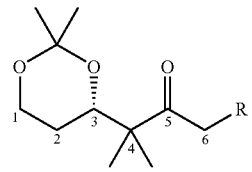

Ia

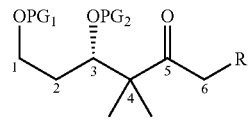

Ib

These compounds (fragments) can be present in form Ia with a cyclic ketal protective group or the open form Ib. In this connection, R stands for a C1-C4-alkyl radical, such as the methyl, ethyl-, n- or i-propyl-, n-butyl- or tert.-butyl radical or a C2-C4-alkenyl radical, such as the vinyl or allyl radical. $PG_1$ and $PG_2$ stand for the protective groups that are familiar to one skilled in the art for a hydroxy function, such as, e.g., the methoxymethyl-, methoxyethyl-, ethoxyethyl-, tetrahydropyranyl-, tetrahydrofuranyl-, trimethylsilyl-, triethylsilyl-, tert.-butyldimethylsilyl-, tert.-butyldiphenylsilyl-, tribenzylsilyl-, triisopropylsilyl-, methyl-, tert.-butyl-, benzyl-, para-nitrobenzyl-, para-methoxybenzyl-, formyl-, acetyl-, propionyl-, isopropionyl-, butyryl-, pivalyl-, or benzoyl radical.

The TBDMS group or other silyl protective groups are preferred.

A survey of the protective groups is found in "Protective Groups in Organic Synthesis" Theodora W. Green, John Wiley and Sons).

PRIOR ART

Production of the epothilone C1-C6 segment of formula III is described in Patent Applications WO 03/04063 and WO 03/015068. In this case, the starting compounds of type IIa or type IIb are converted in an organometallic reaction with an alkyl metal to a compound of formula III.

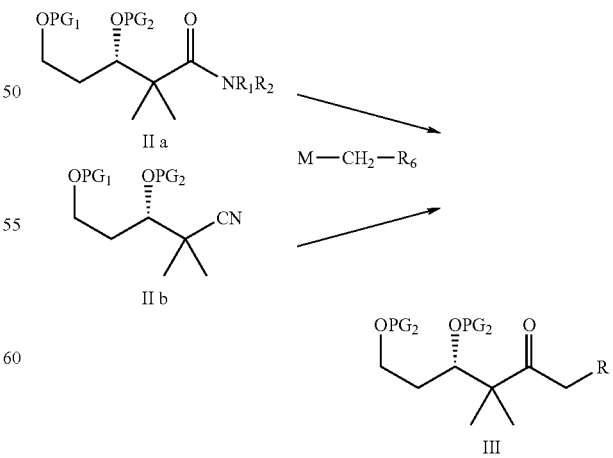

M = Li, MgX, X = Cl, Br, I
$R_6$ = Alkyl, alkenyl, alkinyl, etc., see description The conversion of the dialkylamide group into IIa or the nitrile group into IIb can be carried out in a smooth reaction in a synthesis stage to form III.

After the hydrolysis of the reaction mixture, the product of formula III is obtained in a high yield. In comparison to this, the direct reaction of an organometallic compound with an alkyl ester function —$CO_2R^a$ is not selective since the intermediately produced ketone is further reacted. In the case of the primary adducts from IIa or IIb, the latter are stabilized and react no further to the carbinol in question as the secondary reaction.

The addition of a radical —$CH_2R_a$ to a nitrile can be more advantageously performed with alkyl lithium compounds as a reagent than with organomagnesium compounds. Thus, a process with EtMgBr that is described in US 2002/0156289A1 (The University of Kansas, USA) yields a ketone in a yield of only 56%, while the reaction with methyl lithium proceeds in a yield of 98%.

Drawbacks of the Prior Art

The availability of lithium organyl compounds and organometallic compounds is limited. Therefore, it would be advantageous if it is possible to use standard lithium organyl compounds, which are commercially available or can be produced in a simple way. With the latter, another alkyl radical should be introduced in a subsequent alkylation step via α-alkylation of the methyl ketone of formula IIIa. This would then be especially advantageous if the alkyl halide or alkenyl halide that is based on the organometallic compound is quite costly or not available, as is the case, for example, in the C4-C6-alkenyl halides.

For example, in the case of a homoallyl radical that is to be introduced, the underlying homoallyl bromide is very costly. Also, the production of, e.g., but-3-en-1-yl lithium provides technical problems. In practice, the reaction of 1-bromobut-3-ene to but-3-en-1-yl lithium is accompanied by the elimination of buta-1,3-diene.

In the cases in which the organometallic compounds are not accessible, it may be more advantageous if an intermediate compound of formula IIa or IIb is reacted with a standard alkyl reagent, such as, e.g., methyl lithium, whereby a compound of form IIIa ($R^6$=H) is obtained.

In a subsequent step, the alkylation is carried out with a suitable alkylating agent in the presence of a base to form a compound of form IVa. The bis-alkylating product of formula IVb is undesirable in any case.

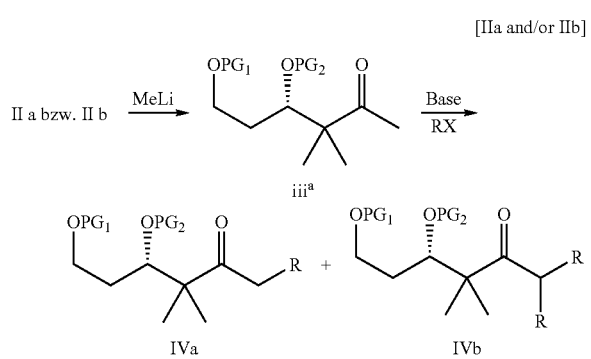

The alkylation of alkyl ketones of formula IIIa to the chain-lengthened alkyl ketones of formula IVa in practice requires special reaction conditions. Often, in this respect, complexing agents are necessary for stabilizing the metal enolate. In 1965, House (J. Org. Chem. 1965, 30, 1341-1348) described that the alkylating reaction results in a reprotonation, and the bis-alkylation is in competition with the monoalkylation. House postulated that the less-substituted enolate is present in aggregated state on an enlarged scale and is also less reactive. The desired monoalkylation requires that in the reaction after deprotonation of the α-carbon atom, no re-metallization of the carbanion is carried out.

In addition to the desired monoalkylation product, in general the bis-alkylation product IVb also is produced; often the conversion is incomplete, such that starting material also remains. As an additional secondary reaction, condensation reactions can also occur in the alkylation reaction. The reaction products such as monoalkylation product IVa, bis-alkylation product IVb and starting material of formula IIIa are generally very expensive to separate.

The problem of bis-alkylation has been described by, i.a., A. Streitwieser et al. in Org. Lett., 2001, 3, 2599-2601. In the purification, there is a problem in that the reaction mixture that consists of starting material, monoalkylation product and bis-alkylation product can be separated.

OBJECT OF THE INVENTION

With this invention, a process should be made available that makes it possible to obtain only the monoalkylation product in IV a in a simple way in the alkylation of IIIa. The epothilone-segment C1-C6 (=monoalkylation product IV a) is a molecule with a high value, in which a high yield and high purity can be targeted.

Achievement of the Object of this Invention

The problem of selective alkylation is achieved according to the invention in that a β-keto ester of general form V is produced from a compound of general formula IIIa. Keto esters of general formula V offer access to the compounds of general formula VI, which after saponification to VII and decarboxylation of the ester group yields the product of formula IVa.

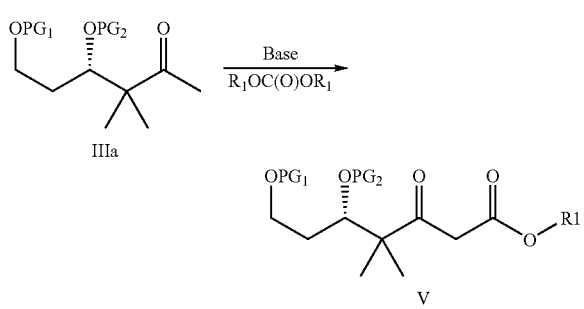

The compounds of general formula V can be produced according to known methods from a compound of general formula IIIa and an ester of the carboxylic acid, preferably dimethyl carbonate or diethyl carbonate. As a base, for example, sodium methylate, sodium ethanolate, potassium-tert-butanolate or sodium hydride is used. As a solvent, in addition to solvents such as THF, dioxane, etc., the carbonate itself can be used simultaneously.

The alkylation of a β-keto ester is a standard method for alkylation of carbanions. By two adjacent activating carbonyl groups, the α-carbon is quite easy to deprotonate and is generally readily alkylated (A. C. Cope; H. L. Holmes; H. O. House, Org. React. 1957, 9, 107-331).

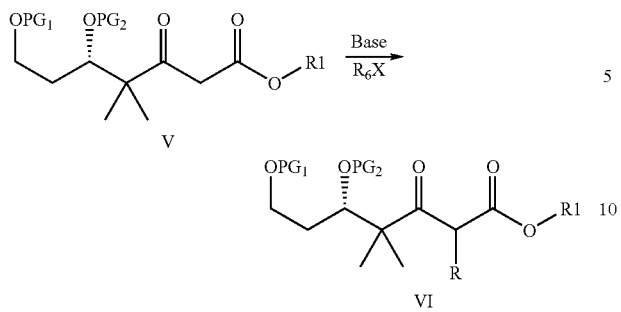

V

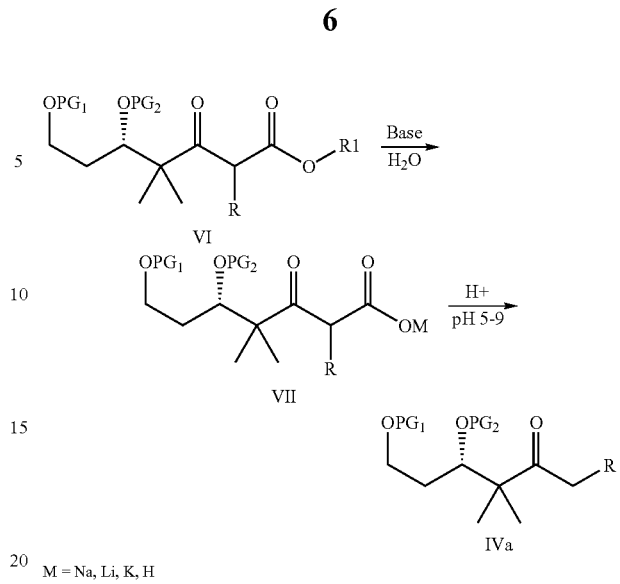

M = Na, Li, K, H

It has been shown that the keto esters of formula V can be readily alkylated to form compounds of general formula VI. As bases, in this respect, metal hydroxides such as sodium, lithium, potassium or calcium hydroxide; metal hydrides such as sodium or lithium hydride; amine bases such as LDA (lithium diisopropylamide), sodium amide, LiHMDS (lithium hexamethyl disilazane); metal alkoxides, such as, e.g., sodium methylate, sodium ethylate and alkali alcoholates of higher alcohols (alkali=lithium, sodium, potassium) are suitable.

$R^6$ in $R^6X$ and thus in general formulas IIIa, IVa, VI and VII has the meaning of $C_1$-$C_6$-alkyl, $C_2$-$C_6$-alkenyl or $C_2$-$C_6$-alkinyl. $C_1$-$C_6$ Alkyl can be straight-chain or branched; $R^6$ can also mean an alkoxyalkyl-, alkoxy-alkenyl, alkoxy-alkinyl and even aryl-alkyl, in which alkyl in the alkoxy part means a $C_1$-$C_6$-alkyl radical and aryl means a phenyl- or naphthyl radical, and -alkyl, alkenyl-, and alkinyl stand for a $C_1$-$C_6$-alkyl, $C_2$-$C_6$-alkenyl or $C_2$-$C_6$-alkinyl radical.

In particular, $R^6$ stands for the radical allyl, crotyl and benzyl.

The alkylation can be performed with the corresponding alkyl halides, allyl halides, benzyl halides, tosylates and alkyl sulfur ester derivatives of formula $R^6X$ that yield the radical $R^6$. As alkylating agents, preferably alkyl chlorides, alkyl bromides, alkyl iodides, as well as alkyl esters of sulfuric acid and alkyl esters of alkyl sulfonic acids or aryl sulfonic acids are used.

Surprisingly enough, in the case of alkylation with allyl halides or benzyl halides, no multiple alkylation is observed. The reactions can be readily tracked analytically (GC, DC, HPLC). After the reaction has taken place, the reaction can be completed by adding sodium hydroxide to the reaction solution.

The process according to the invention has the advantage that no costly complexing agents, such as, e.g., DMPU (dimethyl propylene urea), are required. Also, no low-temperature conditions are necessary for the alkylation. The alkylation can be performed in a temperature range of between 0° C. and 50° C. Also, the reactions are robust and not very sensitive relative to the moisture and the presence of air. In the case of incomplete conversion, base and alkylating agents can be yielded. Condensation products do not occur by self-condensation.

As an alternative to the intermediate isolation of the compounds of general formula VI, the possibility exists of directly saponifying the latter without intermediate isolation. This preferably takes place by adding an aqueous solution of sodium hydroxide or potassium hydroxide to the reaction solution with the compound of general formula VI, whereby a substance of formula VII is obtained.

By acidification and controlled heat treatment of the solution of a compound of general formula VII, a compound of general formula IVa is obtained with decarboxylation.

The acidification is preferably carried out with phosphoric acid or ammonium chloride solution; the acidification is carried out with pH monitoring.

The process is characterized in that the substances are stable in a specific pH range relative to a possible protective group cleavage or else ketal cleavage (in the case of PG1/PG2=ketal group).

The compounds of general formula IVa are surprisingly stable in the alkaline range.

At temperatures of up to 100° C., the compounds of general formula VII can be reacted for decarboxylation.

It has been found that the decarboxylation can be performed at a pH of 4-9. The pH is decisive for the stability of the protective groups in the decarboxylation. The compounds of formulas II, IVa, V and VI can be further reacted without intermediate isolation in solution.

One advantage is the quality of the product that is produced according to this process, which contains less than 1 percent of educt IIIa and less than 1% of bis-alkylated compound IVb.

Based on the high quality of crude product IVa, a simple purification of the crude product is possible by, e.g., distillation.

The compounds of general formula VI can also be reacted directly to form the compounds of general formula IVa, by the compounds of general formula VI being reacted with lithium carbonate in DMF (dimethylformamide) at approximately 100° C. with the addition of water. This reaction is referred to as dealkoxycarbonylation, whereby $CO_2$ is cleaved off, and an alkyl bromide is formed.

The compounds of formula VI can also be produced from a compound of general formula IIb and a bromine ester of general formula VIII in a Reformatsky-type reaction with zinc under the action of ultrasound (K. Nakunan, B.-J. Uang, Synthesis 1989, 571).

In the compounds of general formulas VI and VIII, R1 and R6 already have the meanings that are indicated in general formula VI.

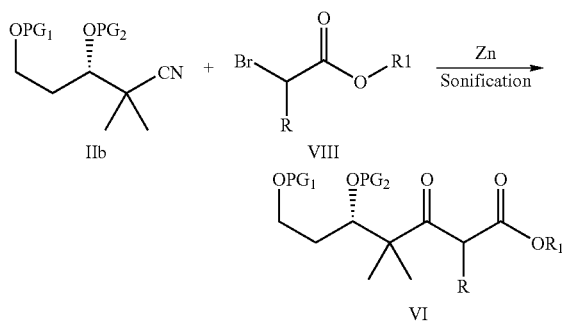

In the case of the synthesis of allyl-substituted compounds with R6=allyl, the allyl esters of general formula IX can be used for synthesis in the case of the compounds of formula VI.

One method for synthesis of IX is the reaction of a compound of general formula IIIa by reaction with diallyl carbonate in the presence of a base.

The alkyl keto esters of formula IX are also accessible, for example, by reesterification of, for example, an alkyl ester of general formula V.

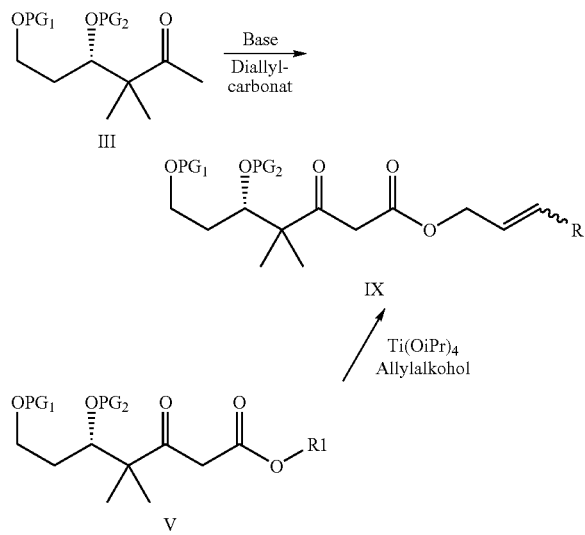

[Key:
Diallylcarbonat = Diallyl Carbonate
Alkylalkohol = alkyl alcohol]

The allyl keto esters of general formula IX can also be converted in a rearrangement reaction into the homoallyl ketone of general formula X.

In the literature, this reaction is referred to as the Carroll reaction (M. F. Carroll, J. Chem. Soc. 1940, 1226). The Carroll reaction can also be referred to as a [3,3]-sigmatropic rearrangement. For reaction, an allyl keto ester is heat-treated. The thermal rearrangement of allyl esters requires high temperatures (170-200° C.). A limitation of the method is often provided by the low heat resistance of the compounds.

In the presence of bases, this rearrangement is promoted and can be performed at milder temperatures (see J. Org. Chem., 1987, 52, 2988-2995). According to method A, an aluminum alkoxide, such as, e.g., Al(OiPr)$_3$ (aluminum-tri-isopropylate) preferably can be used.

This reaction of IX to X can also be performed in such a way that an alkyl ester of general formula IV is reesterified in the presence of a base, whereby the subsequent reaction takes place with the simultaneous rearrangement and decarboxylation in the presence of aluminum alkoxides according to A) the introduction of the allyl group.

Such palladium-catalyzed decarboxylations/allylations have been described by J. Tsuji et al. in J. Org. Chem., 1987, 52, 2988-2995.

According to this method, allyl esters of general formula IX can be converted under decarboxylation and simultaneous allylation into a homoallyl ketone of general formula X.

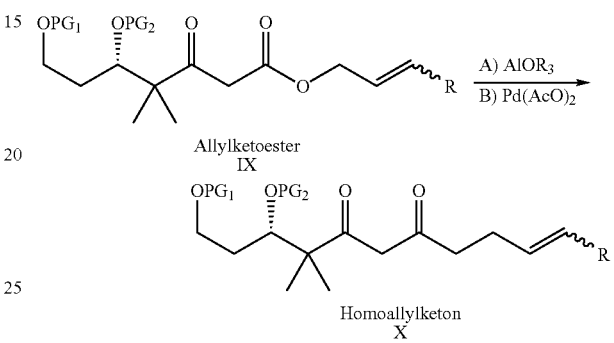

[Key:
Allylketoester = Allyl keto ester
Homoallylketon = Homoallyl ketone]

$R^b$ in general formulas IX, X and XI can have the meaning of hydrogen or a straight-chain or branched-chain $C_1$-$C_6$-alkyl radical, such as, e.g., a methyl, ethyl or propyl radical.

The double bond in compounds of general formula X can be converted with hydrogen with use of a palladium or platinum catalyst into the saturated form of the compounds of general formula XI.

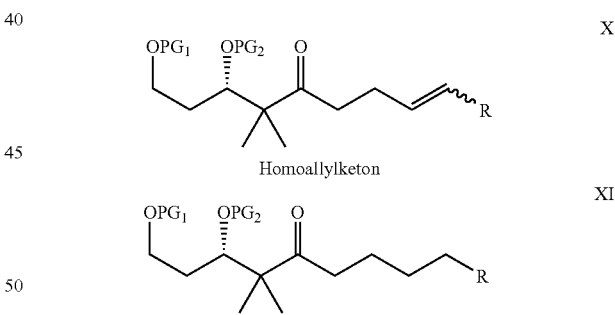

[Key:
Homoallylketon = Homoallyl ketone]

In addition to the compounds of general formulas V, VI, VII, IX and X, this invention also relates to the process that is described here for their production.

The examples that are cited below for a more detailed explanation of this invention relate to the compounds in the natural 3S series. In addition to the 3S enantiomers, the 3R enantiomers and the racemates of the compounds of general formulas V, VI, VII, IX and X are also claimed.

In all structures of formulas II to X, $PG_1$ and $PG_2$ can have the meanings initially mentioned under the compounds of general formulas Ia and Ib; together, they can also mean the isopropylidene group or any ketal structure as a protective group.

By combining the reaction steps of the addition of methyl lithium at II to IIIa, synthesis of the β-keto ester of formula V, selective subsequent alkylation to keto esters of formula VI and subsequent decarboxylation to VII, it was possible to obtain the compounds of formula IVa. The problem of selective alkylation was achieved in this case. The products are obtained in a good yield and high purity. These individual reaction steps can be performed separately in succession or else in a single-pot reaction without intermediate isolation of the intermediate compounds V, VI, VII, and IX.

The process according to the invention makes possible the selective monoalkylation of alkyl ketones. In this case, it is possible to introduce different alkyl radicals, which are not available as organometallic compounds or are not accessible or are difficult to access. The problem for synthesis of homoallyl ketones of formula X could be solved in this case.

This invention is explained in more detail based on the examples below:

EXAMPLE 1

S-3-(2,2-Dimethyl-[1,3]dioxan-4-yl)-3-methyl-butan-2-one 1000 ml of methyl lithium-lithium bromide complex (1.5 M in diethyl ether) is added in drops at −20° C. to 183 g (1 mol) of the title compound of WO 03/014068 (Example 1e) 3(S)-(3,5) acetone dimethyl ketal-2,2-dimethyl-pentane-nitrile, dissolved in 400 ml of THF. Then, it is stirred for 30 minutes at −20° C. and then heated to room temperature. It is stirred for 2 hours at room temperature. 500 ml of saturated ammonium chloride solution is added, and it is stirred for 6 hours while the pH is monitored at room temperature. The product is extracted with hexane, the organic phase is separated, and it is washed twice with water. The organic phase is evaporated to the dry state in a vacuum.

Yield: 195 g (98% of theory) of an oil.

Elementary Analysis:

|  | C | H |
|---|---|---|
| Cld. | 65.97 | 10.07 |
| Fnd. | 65.89 | 10.11 |

EXAMPLE 2

S-3-(2,2-Dimethyl-[1,3]dioxan-4-yl)-4-methyl-3-oxo-pentanoic Acid Methyl Ester 47.5 g (1.118 mol) of 60% paraffin-stabilized sodium hydride is washed paraffin-free with 200 ml of hexane, and 285 ml of THF is added. 338 g (3.76 mol) of dimethyl carbonate is added. 95 g of S-3-(2,2-dimethyl-[1,3]dioxan-4-yl)-3-methyl-butan-2-one in 300 ml of THF from Example 1 is added thereto. The solution is stirred for 1 hour at 67° C. After 1 hour, the reaction is completed by means of thin-layer monitoring (eluant ethyl acetate/hexane 1+1 v/v). To decompose excess NaH, 1.18 mol (71.2 g) of acetic acid is added at room temperature. 300 ml of water is carefully added while being stirred, and it is stirred until the gas generation is completed. The pH is to be in the 7-8 range. The product is extracted with methyl-tert-butyl ether, washed with saturated sodium bicarbonate solution and evaporated to the dry state. 122.3 g (99% of theory) of product is obtained as a viscous oil.

Elementary Analysis:

| MW 258.31 C13H22O5 | C | H |
|---|---|---|
| Cld. | 60.44 | 8.58 |
| Fnd. | 60.7 | 8.6 |

EXAMPLE 3

S-3-(2,2-Dimethyl-[1,3]dioxan-4-yl)-4-methyl-3-oxo-pentanoic Acid Ethyl Ester

Analogously to Example 2, S-3-(2,2-dimethyl-[1,3]dioxan-4-yl)-4-methyl-3-oxo-pentanoic acid ethyl ester is produced from the compound of Example 1 and diethyl carbonate.

Elementary Analysis:

| MW 272.336 C14H24O5 | C | H |
|---|---|---|
| Cld. | 61.73 | 8.88 |
| Fnd. | 61.5 | 8.7 |

EXAMPLE 4

S-3-(2,2-Dimethyl-[1,3]dioxan-4-yl)-4-methyl-3-oxo-pentanoic acid allyl ester

Analogously to Example 2, S-3-(2,2-dimethyl-[1,3]dioxan-4-yl)-4-methyl-5-oxo-pentanoic acid allyl is produced from the compound of Example 1 and diallyl carbonate.

Elementary Analysis:

| MW 298.38 C16H26O5 | C | H |
|---|---|---|
| Cld. | 64.4 | 8.79 |
| Fnd. | 64.5 | 8.81 |

EXAMPLE 5

S-3-(2,2-Dimethyl-[1,3]dioxan-4-yl)-4-methyl-3-oxo-pentanoic Acid Allyl Ester 5.16 g (20 mmol) of S-3-(2,2-dimethyl-[1,3]dioxan-4-yl)-4-methyl-3-oxo-pentanoic acid methyl ester from Example 2 is stirred in 100 ml of allyl alcohol and 1 ml of titanium tetraisopropylate for 6 hours at 80° C. The allyl alcohol is distilled off, the residue is taken up in 100 ml of ethyl acetate and hydrolyzed with 20 ml of water. It is extracted with ethyl acetate, and the organic phase is filtered on 20 g of silica gel. After the residue is concentrated by evaporation, 5.7 g (96% of theory) is obtained as an oil.

EXAMPLE 6

(4S)-4-(2-Methyl-3-oxo-hept-6-en-2-yl)-2,2-dimethyl-[1,3]dioxane 2.84 g (10 mmol) of S-3-(2,2-dimethyl-[1,3]dioxan-4-yl)-4-methyl-3-oxo-pentanoic acid allyl ester from Example 4 is stirred with 80 mg of tetrakis-triphenylphosphine palladium in 20 ml of toluene for 10 minutes at 100° C. After cooling, it is filtered on silica gel, rewashed with methyl-tert-butyl ether and dried. 2.5 g of product (88% of theory) is obtained.

Elementary Analysis:

| MW 284.35 C15H24O5 | C | H |
|---|---|---|
| Cld. | 63.35 | 8.52 |
| Fnd. | 63.5 | 8.6 |

EXAMPLE 7

(4S)-4-(2-Methyl-3-oxo-hept-6-en-2-yl)-2,2-dimethyl-[1,3]dioxane 2.84 g (10 mmol) of S-3-(2,2-dimethyl-[1,3]dioxan-4-yl)-4-methyl-3-oxo-pentanoic acid allyl ester from Example 4 is stirred in 20 ml of toluene with 1 mmol of aluminum triisopropoxide for 1 hour at 100° C. After cooling, it is added to 10 ml of water, the product is extracted with methyl-tert-butyl ether, and it is dried on sodium sulfate. After ball tube distillation at 100° C./1 mbar, 2.3 g of product is obtained as an oil (81% of theory).

EXAMPLE 8

S-3-(2,2-Dimethyl-[1,3]dioxan-4-yl)-3,5-dimethyl-3-oxo-pentanoic Acid Methyl Ester 5.17 g (20 mmol) of S-3-(2,2-dimethyl-[1,3]dioxan-4-yl)-4-methyl-3-oxo-pentanoic acid methyl ester is mixed in 18 ml of ethanol at 0°-10° C. with 2.47 g (22 mmol) of potassium tert-butylate, and it is stirred for 10 minutes. At 20° C., 1.3 ml (3.08 g, 21 mmol) of methyl iodide is added, whereby the temperature increases to 30° C. It is further stirred for 2 hours, whereby a white solid (NaI) precipitates. The reaction is tracked by means of thin-layer chromatography in this case.

Two-thirds of the solution are further reacted in Example 9. The remaining third is neutralized with saturated ammonium chloride solution (pH 7), and the product is extracted with ethyl acetate. 1.75 g of product (96% of theory) is obtained as an oil.

Elementary Analysis:

| MW 274.34 C14H24O5 | C | H |
|---|---|---|
| Cld. | 61.28 | 8.81 |
| Fnd. | 61.5 | 8.9 |

EXAMPLE 9

2-[(4S)-2,2-dimethyl-1,3-dioxan-4-yl]-2-methyl-3-pentanone

Two thirds of the solution of Example 8 (13.4 mmol) are mixed with 20 ml of 2N NaOH (40 mmol) and stirred for 2 hours at 40° C. The saponification is tracked by means of thin-layer chromatography. After saponification, it is neutralized with phosphoric acid ($H_3PO_4$) (pH 7), and the solution is heated under $CO_2$ generation to 80° C. for 30 minutes. After cooling, it is extracted with methyl-tert-methyl ether, and the product is chromatographed. 2.5 g (90% of theory) of product is obtained. The spectroscopic data are identical to the information described in Eur. Chem. J. 2996, 2, 1996, 1477-1482.

EXAMPLE 10

S-3-(2,2-Dimethyl-[1,3]dioxan-4-yl)-4-methyl-5-ethyl-3-oxo-pentanoic Acid Methyl Ester 5.17 g (20 mmol) of S-3-(2,2-dimethyl-[1,3]dioxan-4-yl)-4-methyl-3-oxo-pentanoic acid methyl ester is mixed in 18 ml of ethanol at 0°-10° C. with 2.47 g (22 mmol) of potassium tert-butylate, and it is stirred for 10 minutes. 3.27 g (21 mmol) of ethyl iodide is added at 20° C., and the temperature increases to 30° C. Stirring is continued for 2 hours, whereby a white solid (NaI) precipitates. The reaction is tracked by means of thin-layer chromatography. The reaction is mixed with ammonium chloride solution, extracted with methyl-tert-methyl ester and filtered on silica gel. 4.2 g (92% of theory) is obtained as an oil.

Elementary Analysis:

| MW 286.37 C15H26O5 | C | H |
|---|---|---|
| Cld. | 62.90 | 9.15 |
| Fnd. | 63.01 | 9.09 |

EXAMPLE 11

2-[(4S)-2,2-Dimethyl-1,3-dioxan-4-yl]-2-methyl-3-hexanone 5.17 g (20 mmol) of S-3-(2,2-dimethyl-[1,3]dioxan-4-yl)-4-methyl-3-oxo-pentanoic acid methyl ester from Example 2 is mixed in 18 ml of ethanol at 0°-10° C. with 2.47 g (22 mmol) of potassium tert-butylate, and it is stirred for 10 minutes. At 20° C., 3.27 g (21 mmol) of ethyl iodide is added, whereby the temperature increases to 30° C. Stirring is continued for 2 hours, whereby a white solid (NaI) precipitates. The reaction is tracked by means of thin-layer chromatography. The reaction is mixed with 25 ml of 2N NaOH and stirred for 2 hours at 40° C. After saponification, it is neutralized with phosphoric acid ($H_3PO_4$) (pH 7), and the solution is heated under $CO_2$ generation to 80° C. for 30 minutes. After cooling, it is extracted with methyl-tert-methyl ether, and the product is distilled in a ball tube (boiling point 100° C./1 mbar). 4.1 g (89% of theory) of product is obtained.

Elementary Analysis:

| MW 228.33 C 13H24O3 | C | H |
|---|---|---|
| Cld. | 68.37 | 10.59 |
| Fnd. | 68.35 | 10.4 |

EXAMPLE 12

S-3-(2,2-Dimethyl-[1,3]dioxan-4-yl)-4-methyl-5-benzyl-pentanoic Acid Methyl Ester 5.17 g (20 mmol) of S-3-(2,2-dimethyl-[1,3]dioxan-4-yl)-4-methyl-3-oxo-pentanoic acid methyl ester is mixed in 18 ml of ethanol at 0°-10° C. with 2.47 g (22 mmol) of potassium tert-butylate, and it is stirred for 10 minutes. At 20° C., 3.8 g (30 mmol) of benzyl chloride is added, whereby the temperature increases to 30° C. Stirring is continued for 2 hours, and a white solid (NaI) precipitates. The reaction is tracked by means of thin-layer chromatography. The reaction is mixed with ammonium chloride solution, extracted with methyl-tert-methyl ester, and filtered on silica gel. 6.9 g of product (99% of theory) is obtained as an oil.

Elementary Analysis:

| MW 286.37 C15H26O5 | C | H |
|---|---|---|
| Cld. | 69.93 | 8.1 |
| Fnd. | 69.83 | 8.05 |

EXAMPLE 13

2-[(4S)-2,2-Dimethyl-1,3-dioxan-4-yl]-2-methyl-3-pentanone 5.17 g (20 mmol) of S-3-(2,2-dimethyl-[1,3]dioxan-4-yl)-4-methyl-3-oxo-pentanoic acid methyl ester is mixed in 18 ml of ethanol at 0°-10° C. with 2.47 g (22 mmol) of potassium tert-butylate, and it is stirred for 10 minutes. At 20° C., 3.8 g (30 mmol) of benzyl chloride is added, whereby the temperature increases to 30° C. The reaction is tracked by means of thin-layer chromatography. After the conversion is completed, 25 ml of 2N NaOH is added, and it is stirred for 2 hours at 40° C. until the ester is reacted. After the saponification, it is neutralized with phosphoric acid (H3PO4) (pH 7), and the solution is heated under CO2 generation to 80° C. for 30 minutes. After cooling, it is extracted with methyl-tert-methyl ether, and the product is chromatographed on silica gel. 5.64 g (97% of theory) of product is obtained.

Elementary Analysis:

| MW 290.4 C18H26O3 | C | H |
|---|---|---|
| Cld. | 74.44 | 9.02 |
| Fnd. | 74.16 | 9.05 |

EXAMPLE 14

S-3-(2,2-Dimethyl-[1,3]dioxan-4-yl)-2-allyl-4-methyl-3-oxo-pentanoic Acid Methyl Ester 24.55 g (0.22 mol) of potassium tert-butylate is suspended in 200 ml of ethanol. At 20° C., 51.6 g (0.2 mol) of S-3-(2,2-dimethyl-[1,3]dioxan-4-yl)-4-methyl-3-oxo-pentanoic acid methyl ester from Example 2 is added, and it is stirred for 30 minutes at this temperature. 36.29 g of allyl bromide (1-bromopropene) is added, and stirred for 1 more hour at 40° C. It is hydrolyzed with ammonium chloride solution and hydrolyzed with ethyl acetate. The organic phase is washed with water and dried. 60 g (96% of theory) is obtained as an oil.

EXAMPLE 15

(4S)-4-(2-Methyl-3-oxo-hept-6-en-2-yl)-2,2-dimethyl-[1,3]dioxane 31.2 g (0.1 mol) of S-3-(2,2-dimethyl-[1,3]dioxan-4-yl)-2-allyl-4-methyl-3-oxo-pentanoic acid methyl ester from Example 14 is dissolved in 200 ml of ethanol. 125 ml of 2N NaOH is added, and it is stirred for 2 hours at 40° C. The saponification is tracked by means of thin-layer chromatography. It is neutralized with 85% phosphoric acid (pH 7) and heated for 30 minutes to 80° C. to complete the decarboxylation. After cooling to 30° C., the product is extracted with methyl-tert-butyl ether. After purification on silica gel with hexane and an increasing proportion of ethyl acetate, 21.8 g of product is obtained (91% of theory).

The angle of rotation of a sample $[\alpha]_D$ is +11.6° (1% in $CHCl_3$, l=100 mm).

EXAMPLE 16

(4S)-4-(2-Methyl-3-oxo-hept-6-en-2-yl)-2,2-dimethyl-[1,3]dioxane 24.55 g ((0.22 mol) of potassium tert-butylate is suspended in 200 ml of ethanol. At 20° C., 51.6 g (0.2 mol) of S-3-(2,2-dimethyl-[1,3]dioxan-4-yl)-4-methyl-3-oxo-pentanoic acid methyl ester from Example 2 is added and stirred for 30 minutes at this temperature. 36.29 g of allyl bromide (1-bromopropene) is added and stirred for 1 more hour at 40° C. The reaction is tracked by means of thin-layer chromatography.

For saponification, 250 ml of 2N NaOH is added, and it is stirred for 2 hours at 40° C. The saponification is tracked by means of thin-layer chromatography. It is neutralized with 85% phosphoric acid (pH 7) and heated for decarboxylation for 30 minutes to 80° C. After cooling to 30° C., the product is extracted with methyl-tert-butyl ether. After purification on silica gel with hexane and an increasing proportion of ethyl acetate, 43 g of product is obtained (89% of theory).

EXAMPLE 17

(4S)-4-(2-Methyl-3-oxo-heptan-2-yl)-2,2-dimethyl-[1,3]dioxane 24 g (0.1 mol) of (4S)-4-(2-methyl-3-oxo-hept-6-en-2-yl)-2,2-dimethyl-[1,3]dioxane from Example 17 is dissolved in 480 ml of THF. At room temperature, 4.8 g of palladium on carbon (10%) is added. It is hydrogenated at 10 bar of hydrogen for 2 hours until hydrogen absorption is completed. The catalyst is suctioned off, rewashed with THF, and the product is distilled at 95° C./1 mbar. 21 g of product (87% of theory) is obtained.

Elementary Analysis:

| MW 290.4 C18H26O3 | C | H |
|---|---|---|
| Cld. | 70.6 | 9.91 |
| Fnd. | 70.7 | 10.05 |

The invention claimed is:

1. A compound of formula V

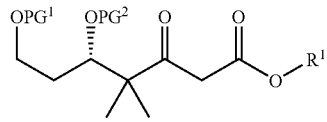

in which
PG$^1$ and PG$^2$ stand for hydroxy protective groups or together for an isopropylidene group, and
R$^1$ stands for a straight-chain or branched-chain, optionally unsaturated hydrocarbon radical with up to 6 carbon atoms.

2. A compound of formula VI

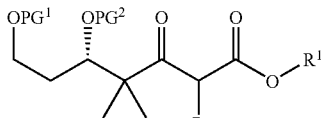

PG$^1$ and PG$^2$ stand for hydroxy protective groups or together for an isopropylidene group, and
R$^1$ stands for a straight-chain or branched-chain, optionally unsaturated hydrocarbon radical with up to 6 carbon atoms, and R$^6$ stands for a C$^1$-C$^6$-alkyl, C$^2$-C$^6$-alkenyl or C$^2$-C$^6$-alkinyl radical, which can be straight-chain or branched, or for an alkoxyalkyl, alkoxy-alkenyl, alkoxyalkinyl or aryl-alkyl radical, in which alkyl in the alkoxy portion means a C$^1$-C$^6$-alkyl radical and aryl means a phenyl or naphthyl radical, and alkyl-, alkenyl-, alkinyl mean a C$^1$-C$^6$-alkyl, C$^2$-C$^6$-alkenyl or C$^2$-C$^6$-alkenyl radical.

3. A compound of formula VII

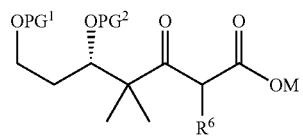

in which
PG$^1$ and PG$^2$ stand for hydroxy protective groups or together for an isopropylidene group, and
R$^6$ stands for a C$^1$-C$^6$-alkyl, C$^2$-C$^6$-alkenyl or C$^2$-C$^6$-alkinyl radical, which can be straight-chain or branched, or for an alkoxyalkyl, alkoxy-alkenyl, alkoxyalkinyl or aryl-alkyl radical, in which alkyl in the alkoxy portion means a C$^1$-C$^6$-alkyl radical and aryl means a phenyl or naphthyl radical, and alkyl-, alkenyl-, alkinyl mean a C$^1$-C$^6$-alkyl, C$^2$-C$^6$-alkenyl or C$^2$-C$^6$-alkenyl radical
and
M stands for a lithium atom or the radical MgX with X in the meaning of a chlorine, bromine or iodine atom.

4. A compound of formula IX

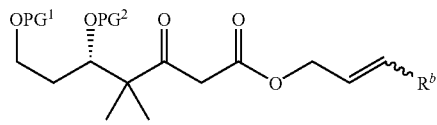

in which
PG$^1$ and PG$^2$ stand for hydroxy protective groups or together for an isopropylidene group, and
R$^b$ stands for a hydrogen atom or a straight-chain or branched-chain C$^1$-C$^6$-alkyl radical.

* * * * *

UNITED STATES PATENT AND TRADEMARK OFFICE
CERTIFICATE OF CORRECTION

PATENT NO. : 7,595,418 B2
APPLICATION NO. : 10/559389
DATED : September 29, 2009
INVENTOR(S) : Westermann et al.

It is certified that error appears in the above-identified patent and that said Letters Patent is hereby corrected as shown below:

On title page Item (54) & Col. 1 lines 1-8 reads "PROTECTED 5,7-DIHYDROXY-4,4-DIMETHYL-3-OXOHEPTANOIC ACID ESTERS AND 5,7-DIHYDROXY-2-ALKYL-4,4-DIMETHYL-3-OXOHEPTANOCI ACID ESTERS FOR THE SYNTHESIZING OF EPOTHILONE AND EPOTHILONE DERIVATIVES AND PROCESS FOR THE PRODUCTION OF THESE ESTERS" should read -- PROTECTED 5,7-DIHYDROXY-4,4-DIMETHYL-3-OXOHEPTANOIC ACID ESTERS AND 5,7-DIHYDROXY-2-ALKYL-4,4-DIMETHYL-3-OXOHEPTANOIC ACID ESTERS FOR THE SYNTHESIZING OF EPOTHILONE AND EPOTHILONE DERIVATIVES AND PROCESS FOR THE PRODUCTION OF THESE ESTERS --.

Signed and Sealed this

Sixteenth Day of March, 2010

David J. Kappos
*Director of the United States Patent and Trademark Office*